US010702206B2

(12) United States Patent
Vetter et al.

(10) Patent No.: US 10,702,206 B2
(45) Date of Patent: Jul. 7, 2020

(54) TOOTHBRUSH FOR ORAL CAVITY POSITION DETECTION

(71) Applicant: Braun GmbH, Kronberg (DE)

(72) Inventors: Ingo Vetter, Hessen (DE); Alexandre André Halbach, Battice (BE)

(73) Assignee: BRAUN GMBH, Kronberg (DE)

( * ) Notice: Subject to any disclaimer, the term of this patent is extended or adjusted under 35 U.S.C. 154(b) by 447 days.

(21) Appl. No.: 15/196,012

(22) Filed: Jun. 28, 2016

(65) Prior Publication Data
US 2016/0374609 A1  Dec. 29, 2016

Related U.S. Application Data

(60) Provisional application No. 62/185,720, filed on Jun. 29, 2015.

(51) Int. Cl.
*A61B 5/00* (2006.01)
*A61C 17/16* (2006.01)
(Continued)

(52) U.S. Cl.
CPC .......... *A61B 5/4547* (2013.01); *A46B 5/0025* (2013.01); *A46B 5/0095* (2013.01); *A46B 9/04* (2013.01); *A46B 15/0006* (2013.01); *A46B 15/0008* (2013.01); *A46B 15/0012* (2013.01); *A61B 5/0002* (2013.01); *A61B 5/0534* (2013.01); *A61C 17/16* (2013.01); *A61C 17/221* (2013.01); *A61C 17/222* (2013.01); *A61C 19/04* (2013.01); *A46B 2200/1066* (2013.01); *A61B 5/002* (2013.01); *A61B 5/486* (2013.01);
(Continued)

(58) Field of Classification Search
CPC ... A61B 5/4547; A61B 5/0002; A61B 5/0534; A61B 5/486; A46B 5/0025; A46B 5/0095; A46B 9/04; A46B 15/0008; A46B 15/0002; A46B 15/0006; A46B 15/0012; A61C 17/16; A61C 17/221; A61C 17/222; A61C 19/04
See application file for complete search history.

(56) References Cited

U.S. PATENT DOCUMENTS 942,708 A    12/1909  Blot
3,783,364 A   1/1974  Gallanis et al.
(Continued)

FOREIGN PATENT DOCUMENTS

DE    19506129 A1   8/1996
DE    102008027317  12/2009
(Continued)

OTHER PUBLICATIONS

AA1025Q International Search Report and Written Opinionfor PCT/IB2016/053892 dated Sep. 2, 2016.
(Continued)

*Primary Examiner* — Weilun Lo
(74) *Attorney, Agent, or Firm* — Vladimir Vitenberg

(57) ABSTRACT

A toothbrush handle for providing oral cavity position detection during operation includes a handle body having a longitudinal axis, a receiver body elastically deformable relative to the longitudinal axis, and a three-axis force sensor that is operatively connected to the base portion and configured to obtain three-axis force data for oral cavity position detection during operation.

18 Claims, 6 Drawing Sheets

(51) Int. Cl.
| | | |
|---|---|---|
| *A46B 15/00* | (2006.01) | |
| *A46B 9/04* | (2006.01) | |
| *A46B 5/00* | (2006.01) | |
| *A61B 5/053* | (2006.01) | |
| *A61C 19/04* | (2006.01) | |
| *A61C 17/22* | (2006.01) | |
| *A61B 90/00* | (2016.01) | |

(52) U.S. Cl.
CPC .......... *A61B 5/6887* (2013.01); *A61B 5/7246* (2013.01); *A61B 2090/064* (2016.02); *A61B 2505/07* (2013.01); *A61B 2562/0219* (2013.01); *A61B 2562/0261* (2013.01)

(56) References Cited

U.S. PATENT DOCUMENTS

| | | |
|---|---|---|
| 4,716,614 A | 1/1988 | Jones |
| 5,561,881 A | 10/1996 | Klinger et al. |
| 5,701,629 A | 12/1997 | O'Brien |
| 5,796,325 A | 8/1998 | Lundell et al. |
| 5,864,288 A | 1/1999 | Hogan |
| 5,930,858 A | 8/1999 | Jung |
| 5,944,531 A | 8/1999 | Foley |
| 6,102,284 A | 8/2000 | Myers et al. |
| 6,519,579 B1 | 2/2003 | Plankensteiner et al. |
| 6,536,068 B1 | 3/2003 | Yang et al. |
| 6,611,780 B2 | 8/2003 | Lundell et al. |
| 6,752,627 B2 | 6/2004 | Lin |
| 6,754,928 B1 | 6/2004 | Rosen |
| 6,808,298 B2 | 10/2004 | Christensen |
| 6,902,397 B2 | 6/2005 | Farrell et al. |
| 7,024,717 B2 | 4/2006 | Hilscher et al. |
| 7,411,511 B2 | 8/2008 | Kennish et al. |
| 7,748,069 B2 | 7/2010 | Dawley |
| 7,890,193 B2 | 2/2011 | Tingey |
| 7,976,388 B2 | 7/2011 | Park et al. |
| 8,175,840 B2 | 5/2012 | Hwang et al. |
| 8,176,591 B2 | 5/2012 | Iwahori et al. |
| 8,201,295 B2 | 6/2012 | Gatzemeyer et al. |
| 8,320,682 B2 | 11/2012 | Froeba et al. |
| 8,341,791 B2 | 1/2013 | Iwahori |
| 8,393,037 B2 | 3/2013 | Iwahori et al. |
| 8,479,341 B2 | 7/2013 | Iwahori |
| 8,544,131 B2 | 10/2013 | Braun et al. |
| 8,743,051 B1 | 6/2014 | Moy et al. |
| 8,744,192 B2 | 6/2014 | Ortins et al. |
| 9,174,351 B2 | 11/2015 | Binder |
| 9,848,174 B2 | 12/2017 | Binder |
| 9,950,434 B2 | 4/2018 | Binder |
| 9,950,435 B2 | 4/2018 | Binder |
| 10,064,711 B1 * | 9/2018 | Richter ............... A61C 17/221 |
| 10,220,529 B2 | 3/2019 | Binder |
| 10,449,681 B2 | 10/2019 | Binder |
| 2002/0133308 A1 | 9/2002 | Lundell |
| 2003/0115694 A1 | 6/2003 | Pace |
| 2004/0019990 A1 | 2/2004 | Farrell |
| 2004/0053190 A1 | 3/2004 | Lin |
| 2005/0000044 A1 | 1/2005 | Hilscher et al. |
| 2006/0040246 A1 | 2/2006 | Ding |
| 2006/0096046 A1 | 5/2006 | Hilscher |
| 2007/0136964 A1 | 6/2007 | Dawley |
| 2007/0182571 A1 | 8/2007 | Kennish |
| 2007/0234493 A1 | 10/2007 | Hilscher et al. |
| 2007/0270221 A1 | 11/2007 | Park |
| 2008/0010771 A1 | 1/2008 | Hilscher et al. |
| 2008/0022469 A1 | 1/2008 | Hilscher |
| 2008/0022470 A1 | 1/2008 | Hilscher |
| 2008/0022471 A1 | 1/2008 | Hilscher |
| 2008/0022501 A1 | 1/2008 | Hilscher |
| 2008/0022503 A1 | 1/2008 | Hilscher |
| 2008/0028549 A1 | 2/2008 | Hilscher |
| 2008/0032265 A1 | 2/2008 | Hilscher |
| 2008/0109973 A1 | 5/2008 | Farrell et al. |
| 2008/0196185 A1 | 8/2008 | Gatzemeyer |
| 2008/0313829 A1 | 12/2008 | Dabrowski |
| 2009/0092955 A1 | 4/2009 | Hwang |
| 2009/0130636 A1 | 5/2009 | Hwang |
| 2009/0143914 A1 | 6/2009 | Cook et al. |
| 2009/0291422 A1 | 11/2009 | Puurunen |
| 2009/0317770 A1 | 12/2009 | Gatzemeyer |
| 2010/0281636 A1 | 11/2010 | Ortins |
| 2011/0010875 A1 | 1/2011 | Iwahori et al. |
| 2011/0010876 A1 | 1/2011 | Iwahori et al. |
| 2011/0041269 A1 | 2/2011 | Iwahori |
| 2011/0146016 A1 | 6/2011 | Gatzemeyer et al. |
| 2012/0151697 A1 | 6/2012 | Farrell et al. |
| 2012/0266397 A1 | 10/2012 | Iwahori |
| 2012/0310593 A1 | 12/2012 | Bates et al. |
| 2014/0065588 A1 | 3/2014 | Jacobson et al. |
| 2014/0246049 A1 | 9/2014 | Ikkink et al. |
| 2015/0044629 A1 * | 2/2015 | Wang ................ A46B 15/0006 433/27 |
| 2016/0235357 A1 | 8/2016 | Ohmer |
| 2016/0374609 A1 | 12/2016 | Vetter et al. |
| 2017/0065386 A1 | 3/2017 | Farrell et al. |
| 2017/0069083 A1 | 3/2017 | Vetter et al. |
| 2017/0236298 A1 | 8/2017 | Vetter |
| 2017/0238692 A1 | 8/2017 | Sarubbo |
| 2018/0192765 A1 * | 7/2018 | Jeanne ............... A46B 15/0006 |

FOREIGN PATENT DOCUMENTS

| | | | |
|---|---|---|---|
| DE | 102009048117 A1 | 4/2011 | |
| DE | 102009048118 A1 | 4/2011 | |
| EP | 1593001 B1 | 6/2012 | |
| EP | 2833325 A1 | 2/2015 | |
| EP | 2406697 B1 | 4/2016 | |
| EP | 3141151 A1 | 3/2017 | |
| EP | 3238565 A1 * | 11/2017 | ......... A46B 15/0042 |
| FR | 2832298 A1 | 5/2003 | |
| JP | 09168428 | 6/1997 | |
| JP | 11346833 A | 12/1999 | |
| JP | 2003534095 A | 11/2003 | |
| JP | 2011146049 | 7/2011 | |
| WO | WO2006137648 A1 | 12/2006 | |
| WO | WO2007032015 | 3/2007 | |
| WO | WO2007112112 A1 | 10/2007 | |
| WO | WO2011073010 A1 | 6/2011 | |
| WO | WO2014103412 A1 | 7/2014 | |
| WO | WO2014202438 A1 | 12/2014 | |
| WO | WO2016020803 A1 | 2/2016 | |

OTHER PUBLICATIONS

Bocksch, M. et al. Pedestrian Activity Classification to Improve Human Tracking and Localization. In: Proceedings of the 4th International Conference on Indoor Positioning and Indoor Navigation (IPIN), 2013, S. 667-671.

DeMenthon, D.F. et al. "Model-Based Object Pose in 25 Lines of Code", Computer Vision Laboratory, ECCV 1992, pp. 335-343.

Ernst, A. et al. "Fast face detection and species classification of African great apes", AVSS 2011, IEEE 8th International Conference on Advanced Video and Signal-based Surveillance.

Kueblbeck, C. et al. "Face detection and tracking in video sequences using the modified census transformation", Journal on Image and Visiong Computing, vol. 24, issue 6, pp. 564-572, 2006.

Saragih, J et al. "Deformable Model Fitting by Regularized Landmark Mean'Shifts", International Journal of Computer Vision, 2011 91: 200-215.

* cited by examiner

TOOTHBRUSH FOR ORAL CAVITY POSITION DETECTION

FIELD OF THE INVENTION

The present invention is directed to detecting oral cavity positions of an electric toothbrush during operation.

BACKGROUND OF THE INVENTION

Maintaining good oral hygiene is important for oral health and even overall well-being. Proper and regular tooth brushing is a basic and important part of an oral care regimen. Various toothbrushes, including electric toothbrushes, have been developed to facilitate effective tooth brushing. Researchers have continuously tried to improve the brushing quality, for example, by optimizing the brushing head, increasing the head rotation frequency, designing new cleaning techniques such as by way of ultrasound. Although some of these attempts have been successful in theory and even endorsed by dentists, high brushing quality has not been achieved in practice by many consumers. There are several explanations proposed. For example, at least one study reports that an adult brushes on average for 46 seconds while the recommended brushing time is generally accepted as 2 minutes. Studies even show that during this short brushing time consumers tend to brush unevenly, neglecting certain teeth surfaces and over-brushing others. This possibly leads to cavity formation and/or plaque accumulation in those surfaces where there is not enough brushing, and receding gums where there is too much brushing. Therefore, it is important for the consumer to receive real-time feedback on the brushing position (and time), to optimize their brushing procedure. Such feedback relies on the ability to precisely and accurately detect the position of the toothbrush in the mouth.

There have been efforts in developing position detection technology for about a decade. For example, U.S. Pat. No. 8,393,037 discloses a three-axis acceleration sensor mounted to a body of an electric toothbrush to estimate which portion is being brushed. A load sensor, provided inside the body of the toothbrush, for detecting brush pressure (a load imposed on the brush) is also disclosed. Any type of sensor including a strain gauge sensor, a load cell sensor, and a pressure sensor apparently can be utilized as the load sensor.

US 2012/266397 A1 (2012 Oct. 25) discloses an electric toothbrush estimating a brushing area by measuring the impedance between two electrodes by means of an impedance measuring unit.

U.S. Pat. No. 8,544,131 discloses an oral hygiene implement having a pressure indicator. The implement has a force sensor and an output source. A pivot point may be disposed in the handle, which is apparently beneficial for toothbrushes where the neck or head are replaceable.

However, to date no one has broadly and cost effectively commercialized this technology. There continues to be a need of providing non-intrusive, precise and/or accurate position detection at a low cost. Position detection technology will help users improve their brushing procedure so as to mitigate the occurrence of plaque and caries, as well as gum recession.

SUMMARY OF THE INVENTION

The present invention attempts to address one or more of these needs.

The present invention is based, in part, on the use of a 3-axis force sensor so this 3-axis force sensor data can be used to provide valuable oral cavity position detection to the user for every brushing episode. For example, feedback can be provided to the user whether there is too little or too much brushing in any one oral cavity position (e.g., tooth zone).

One advantage of the present invention is the use of 3-axis force sensor data to additionally provide user feedback about using too much force or not enough force in any one tooth zone. Indeed there is a need to balance between not enough brushing force to enable cleaning but too much force resulting in gum irritation, gum recession, or even tooth enamel abrasion. It is often difficult for users to find the right balance. The use of 3-axis force sensor may provide the additional benefit of providing user feedback on the brushing force sufficiency or insufficiency.

Another advantage of the present invention is the use of a receiver body elastically deformable relative to a longitudinal axis, preferably the elastic deformation is 3-axis elastic deformation (relative to the longitudinal axis). This is contrast to deformation, for example, in only one direction which limits available information that is otherwise available from obtaining information in three dimensions (i.e., x-, y- and z-axis)

Another advantage of the device is the cost and simplicity of providing oral cavity position detection (as well as brushing force feedback) to the user. Position detection accuracy may also be overall improved.

Several aspects of the invention are described. One aspect provides for an electric toothbrush handle for providing oral cavity position detection during operation comprising: a handle body having a longitudinal axis; a receiver body extending from the handle body along said longitudinal axis, wherein the receiver body has: (i) an engaging portion distal the handle body and configured to removably engage a replaceable toothbrush head; and (ii) a base portion opposing the engaging portion, wherein the base portion adjoins the handle body; an electric motor contained in the handle body; a drive shaft, operatively connected to the electric motor, extending along the longitudinal axis from the motor and at least partially into the receiver body. The electric toothbrush handle is further defined by the receiver body elastically deformable relative to the longitudinal axis; and a 3-axis force sensor, operatively connected to the base portion, configured to obtain 3-axis force sensor data for oral cavity position detection during operation. Preferably the 3-axis force sensor comprises at least three strain gauges, preferably at least four strain gauges, operatively and physically connected to a surface of the base portion, preferably to an outside surface of the base portion. Preferably housing houses the operatively and physically connected strain gauges. Preferably the base has a cross sectional shape (relative to the longitudinal axis) of a regular polygon, preferably a tetragon. Preferably the base has a cross sectional area (relative to the longitudinal axis) from 10 mm$^2$ to 40 mm$^2$, preferably from 20 mm$^2$ to 30 mm$^2$ More preferably the base has a cross sectional shape (relative to the longitudinal axis) of a regular polygon, preferably a tetragon; and wherein the base has a cross sectional area (relative to the longitudinal axis) from 10 mm$^2$ to 40 mm$^2$, preferably from 20 mm$^2$ to 30 mm$^2$.

Without wishing to be bound by theory this cross section area is important because if the cross sectional area is too large, then the bending would be to small and then the 3-axis force sensor could not accurately measure typical brushing forces. If however, the cross sectional area is too small, the plastic portion of the base portion could break or plastification becomes too dominant. Preferably the base should be made out of a material (or a combinations of materials) that is used below its plastification level (when considering the brushing forces applied in a typical brushing episode) but which still bends enough to have a sensitive measurement by the 3-axis force sensor. The material(s) should also preferably not have bending properties changing too much with temperature and over time.

Preferably the toothbrush further comprises an accelerometer and gyroscope, contained within the handle body, configured to obtaining 3-axis accelerometer and gyroscope data that can be used to help with oral cavity position detection during toothbrush operation.

Another aspect of the invention provides for a manual toothbrush for providing oral cavity position detection during operation comprising: a handle body having a longitudinal axis; a head comprising one or more static oral care cleaning or massaging elements; a neck extending between the handle body and the head, wherein the head is distal the handle body; a battery (contained in the handle body). The manual toothbrush has at least a portion of the neck elastically deformable relative to said longitudinal axis; a 3-axis force sensor, in electrical communication with the battery, operatively connected to the elastically deformable portion of the neck or head, and configured to providing 3-axis force for oral cavity position detection during operation; and a transmitter, in communication with the 3-axis force sensor, configured to transmit 3-axis force sensor data remotely from the manual toothbrush. Preferably the manual toothbrush is one wherein the 3-axis force sensor comprises at least three strain gauges, more preferably at least four strain gauges, operatively and physically connected to a surface of the flexible portion of the neck or head; even more preferably wherein at least one of the three strain gauges obtain compression or traction force data (along the longitudinal axis). Preferably the manual toothbrush is one further comprising an accelerometer and gyroscope, contained within the handle body, configured to obtaining 3-axis accelerometer and gyroscope data force for oral cavity position detection during operation, and wherein the transmitter, in communication with the accelerometer and gyroscope, is configured to transmit 3-axis accelerometer and gyroscope data remotely from the manual toothbrush. The manual toothbrush is devoid of a motor for moving the head (rather relying upon the user to manually provide the necessary movement).

These and other features, aspects, and advantages of the present invention will become evident to those skilled in the art from the detailed description which follows.

BRIEF DESCRIPTION OF THE DRAWINGS

While the specification concludes with claims particularly defining and distinctly claiming the invention, it is believed that the invention will be better understood from the following description of the accompanying figures.

DETAILED DESCRIPTION OF THE INVENTION

Figure 1:
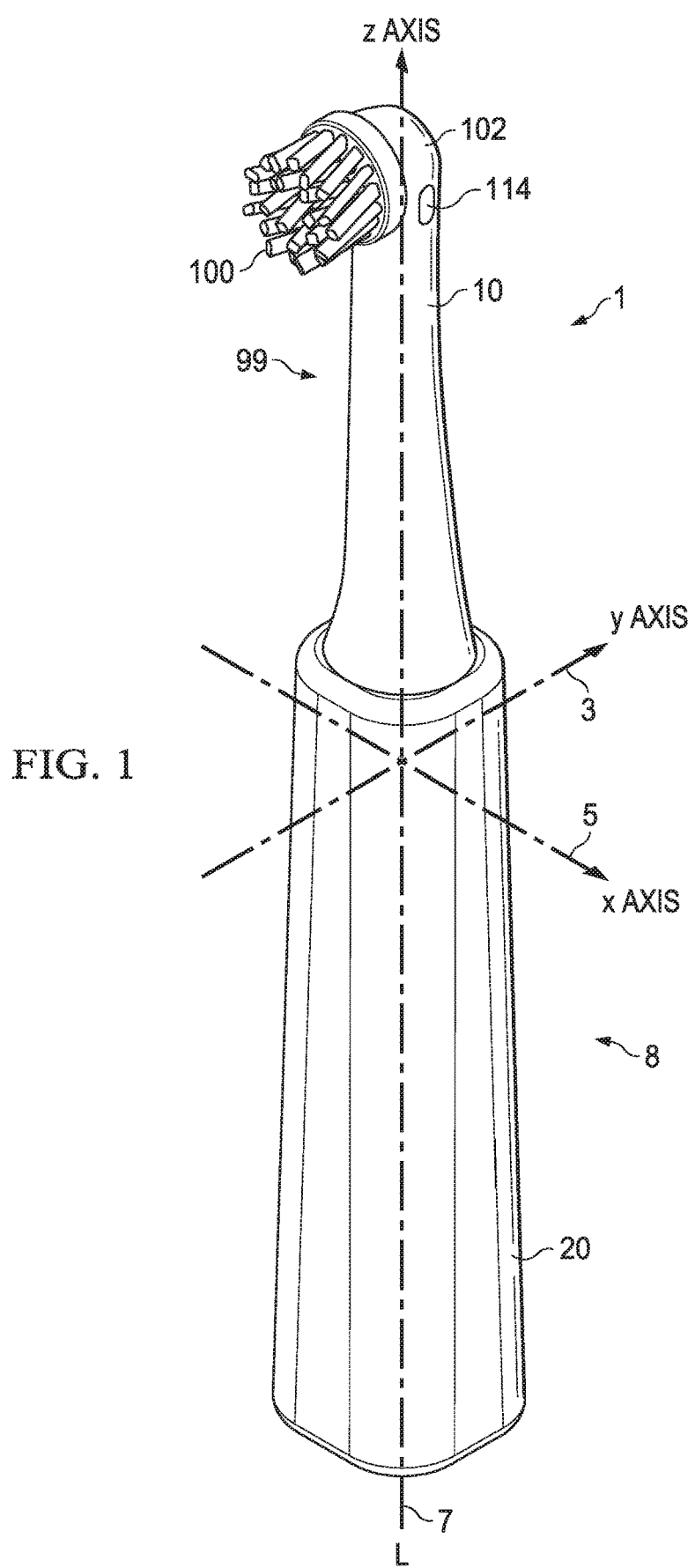
FIG. 1 is a perspective view of an electric toothbrush with housing over a handle body and receiver body and illustrating an arrangement of x-, y-, and z-axis for oral cavity position determination.

As used herein, the articles including "a", "an", and "the" are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

The present invention is generally directed to an electric toothbrush having an electric toothbrush handle, and a replaceable toothbrush head releasably attached thereto. A non-limiting example of such a device is generally described in WO 2010/106524. ORAL B® is a brand of electric toothbrushes.

3-Axis Force Sensor

The present invention is directed to a 3-axis force sensor that is configured to obtain 3-axis force sensor data. A 3-axis force sensor measures bending in two directions: (i) in an x-axis and y-axis direction (wherein the x-axis and y-axis are about 90 degrees from each other and both the x-axis and y-axis are orthogonal to a longitudinal axis of electric toothbrush handle); and (ii) traction or compression forces (i.e., along the longitudinal axis or z-axis). The electric toothbrush handle has a handle body and a receiver body. The handle body contains an electrical motor and battery in electrical communication with the motor. The handle body has a longitudinal axis. A receiver body extends from the handle body along the longitudinal axis. The receiver body, in turn, has an engaging portion and an opposing base portion. The engaging portion removeably engages a replaceable toothbrush head. The base portion adjoins the handle body, while the engaging portion is distal the handle body. In other words, the base portion is in between the handle body and the engaging portion (along the longitudinal axis). The receiver body is elastically deformable relative to the longitudinal axis, preferably elastically deformable in three dimensions (i.e., x-axis, y-axis, and z-axis). The 3-axis force sensor is operatively connected to the base portion, preferably physically and operatively connected to a surface of base portion, preferably an outside surface of the base portion, so as to obtain 3-axis force sensor data during user operation of the electric toothbrush handle (or electric toothbrush containing the same). Housing houses the 3-axis force sensor. Even when the 3-axis force sensor is operatively and physically connected to the base portion, housing houses the 3-axis force sensor so it is protected from exposure and generally from being dislodged during the electric toothbrush's operation. Preferably a single unitary housing houses the entire electric toothbrush handle. An advantage of the present invention is that not only can a 3-axis force sensor data help precisely and accurately detect the position of the electric toothbrush in the oral cavity during operation (i.e., oral cavity position determination), but can also provide feedback on brushing force applied by the user (e.g., too much or too little) at a defined oral cavity position. The use of a 3-axis force sensor data and having the receiver body elastically deformable relative to the longitudinal axis provides important three dimensional oral cavity position determination that otherwise would not be available in two dimensional executions. In some two dimensional executions, the receiver body has a limited range of motion (e.g., use of pivot point or pivot axis) and/or the force sensor failing to obtain 3-axis force sensor data.

The 3-axis force sensor is part of the electric toothbrush handle (distinguished from the replaceable toothbrush head). This way, the user does not need to replace the sensor (or many other electronic components for that matter) each time cleaning or massaging elements (e.g., bristles) become worn. Rather, only the replaceable toothbrush head is replaced. Indeed the sensor has a longer life span than typical cleaning or massaging elements.

Preferably the 3-axis force sensor is miniature in size having a maximum length (i.e., longest dimension) of 7 mm, preferably a maximum length of 5 mm, alternatively less than 5 mm length, alternatively a maximum length from 1 mm to 5 mm. Preferably the 3-axis force sensor is a plurality of strain gauges, wherein the plurality is selected from three to eight strain gauges, preferably 3-5 strain gauges, and alternatively about four strain gauges. Optionally the plurality of the strain gauges are spaced equidistant from each other (physically connected to a surface of the base portion) around the longitudinal axis of the electric toothbrush handle. Preferably 3-axis force sensor is able to measure a range of forces of a magnitude in the order of about 10 N. The 3-axis force sensor may include piezo components. The 3-axis force sensor may also include piezo-resistive pressure-sensors.

Tooth Brush Head

An electric toothbrush is provided having an electric toothbrush handle and a removeably attached replaceable toothbrush head. The replaceable toothbrush head has a head and neck. The neck is configured to removeably attach to the engaging portion of the receiver body (of the electric toothbrush handle). When the toothbrush head is attached, the neck extends between the engaging portion and the head (along the longitudinal axis). The head comprises one or more oral cleaning or massaging elements (e.g., bristles). In a preferred embodiment, the cleaning or massaging elements are protruding in a direction orthogonal to the longitudinal axis (of the electric toothbrush handle). The neck has a neck terminus immediately adjacent the head. The head, with it cleaning or massaging elements, exhibits motion (e.g., rotation, oscillation, vibration) so as to clean or massage teeth and/or gum during operation. The neck (of the replaceable toothbrush head) is preferably much small in diameter than the handle body (of the electric toothbrush handle).

Handle Body

The handle body, of the electric or manual toothbrush handle, is where the user typically grasps during operation of the device. In an electric toothbrush, the handle body contains the electric motor. The electric motor, in turn, provides mechanical movement to the head. A drive shaft is operatively connected to the electric motor. The drive shaft extends along the longitudinal axis (of the handle body) from the motor at least partially into the receiver body, preferably extending through the entire receiver body. When the replaceable toothbrush head is operatively and removeably attached to the electric toothbrush handle, the driver shaft will transfer the movement from the motor to the head—either directly or indirectly via the neck. The handle body contains a battery, preferably a rechargeable battery. The battery is in electrical communication to at least the electric motor and preferably the other electrical components of the device (such as the 3-axis force sensor) to provide power. Notwithstanding the 3-axis force sensor, the handle body may contain one or more of these electric components. The handle body may contain a manual or automatic "on/off" switch for the powering on the device for operation and off when not in use.

Receiver Body

The receiver body has an engaging portion and an opposing base portion. It is the base portion that the 3-axis force sensor is operatively connected. Preferably the 3-axis force sensor is operatively connected to an outside surface of the base portion. In a preferred embodiment, the 3-axis force sensor comprises at least three strain gauges, more preferably at least four strain gauges, physically connected to a surface of the base portion, preferable an outside surface of the base portion, and spaced circumferentially around the base portion (relative to the longitudinal axis). The base portion may have one of any number of cross sectional shapes (relative to the longitudinal axis). For example, the cross sectional shape may be circular or of a regular or irregular shaped polygon. Regular shaped polygons may include a tetragon, pentagon, hexagon, and the like. In a preferred embodiment, the cross sectional shape is a regular tetragon (i.e., four sides with a 90° interior angle), wherein a plurality of strain gauges are physically connected to the outside surface of the receiver body on each of the four sides. The cross section (of the base portion inside the housing where the strain gauges can be physically attached) may have a cross sectional area from 10 $mm^2$ to 50 $mm^2$, preferably from 15 $mm^2$ to 35 $mm^2$, alternatively from 20 $mm^2$ to 30 $mm^2$ These dimensions are exclusive of any housing or any attached strain gauges.

FIG. 1 is an electric toothbrush (1). The toothbrush (1) has an electric toothbrush handle (20) and a replaceable toothbrush head (99). The electric toothbrush handle (20) has a longitudinal axis L (20). The z-axis (20) is the same as the longitudinal axis L (20). Both the y-axis (3) and x-axis (5) are orthogonal to the z-axis (2). In turn, the y-axis (3) and x-axis (5) are 90° relative to each other. A receiver body (13) extends from the handle body (11) along the longitudinal axis L (7). The receiver body (13) has an engaging portion (15) distal the handle body (11) and configured to removably engage a replaceable toothbrush head (99). A base portion (17), opposing the engaging portion (15), adjoins the handle body (11). The replaceable toothbrush head (99) has a head (102) and a neck (10), wherein the neck (10) extends between the engaging portion (15) and the head (102). The head (102) has one or more oral care cleaning or massaging elements (100). An electrode (114) (of an electrode pair) is provided on the head (102). Housing (8) houses the internal components of the electric toothbrush (1). Although not shown in FIG. 1, an electric motor is contained in the handle body (11). A drive shaft (19), operatively connected to the electric motor, extends along the longitudinal axis L (7) from the motor and at least partially into the receiver body (13).

Figure 2:
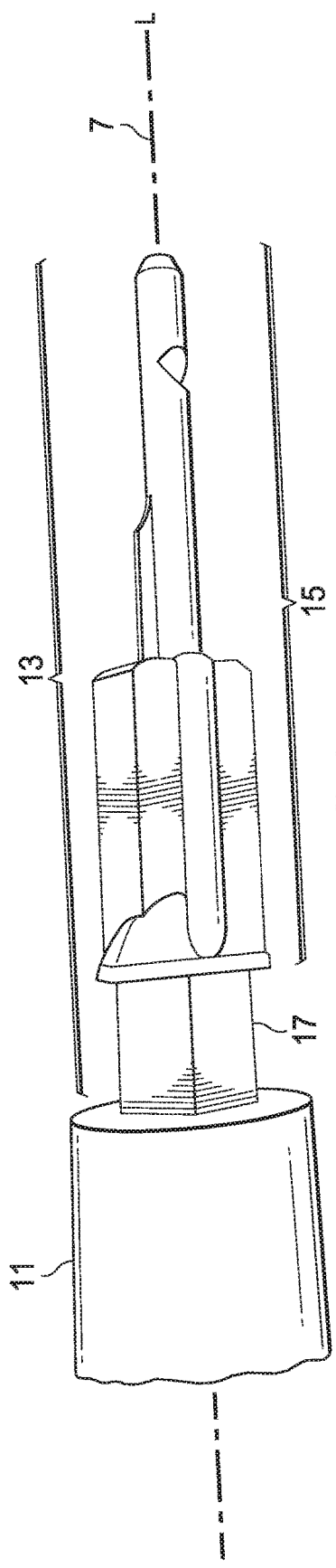
FIG. 2 is a side view of a milled outside surface of the base portion of the receiver body (with housing removing).
Figure 3:
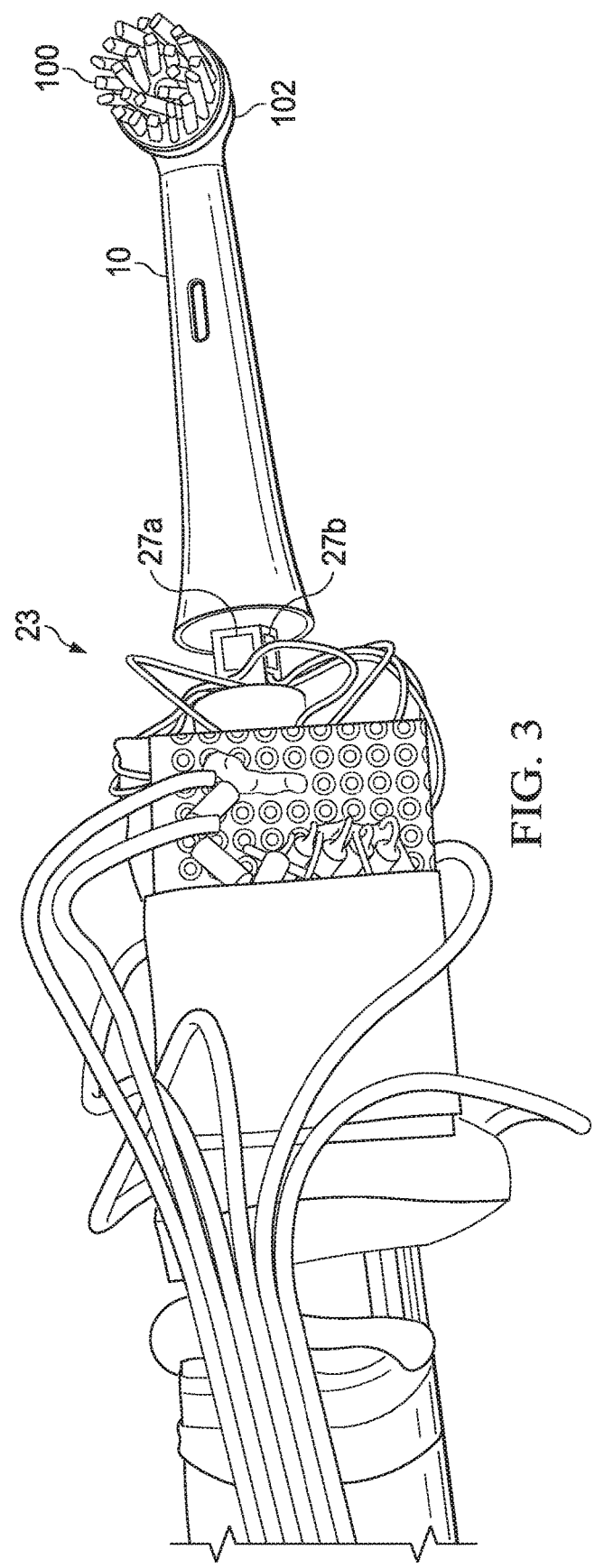
FIG. 3 is a perspective view of an electric toothbrush with four strain gauges operatively and physically connected to the outside surface of the base portion (of previous FIG. 2; and also with the housing removed).

Turning to FIG. 2, in a prototype of the present invention, an ORAL B® TRIUMPH electric toothbrush handle (20), with housing removed, is shown. The engaging portion (15) and opposing base portion (17) of the receiver body (13) is exposed. The base portion (17) is milled to provide 5 mm by 5 mm tetragon cross sectional surface. As illustrated in FIG. 3, a 3-axis force sensor (23) is operatively connected to the base portion (17) (preferably to an outside surface of the base portion (17)) and configured to obtain 3-axis data for oral cavity position detection during operation. In FIG. 3, a total of four strain gauges (27) are placed, i.e., one strain gauge on each of the four surfaces (of the base portion (17)). Although not shown, the base portion (17) has a cross section (relative to the longitudinal axis) in the shape of a tetragon. The cross section has a cross sectional area of about 25 $mm^2$. A first strain gauge (27*a*) and a second strain gauge (27*b*) are visible in FIG. 3 (although it's preferable to a have a total of four strain gauges, with a single strain gauge on each of the four facets of the base portion). One non-limiting example of a strain gauge is KFH-06-120-C1-11L3M3R (pre-wired) from OMEGA. FIG. 3 shows the strain gauge attached to the prototype. Each of the four strain gauges, in the device of FIG. 3, is wired to a Wheatstone bridge through a three-wire connection that helps against wire resistance and connection resistance problems. The Wheatstone bridge's output voltage is connected to an inverting amplifier with a 50 gain. One of the resistors in the Wheatstone bridge is the strain gauge, varying around 120Ω, and the three other resistors are three standard 120Ω resistors. Alternatively, the resistors can be substituted by unconstrained 120Ω strain gauges (so that they have the same characteristics as the measuring strain gauge in each bridge).

Turning back to FIG. 2, the drive shaft (19) extends along the longitudinal axis L (7) from the motor (not shown) and through the receiver body (13). The electric toothbrush handle (20) is characterized, at least in part, by the receiver body (134) being elastically deformable relative to the longitudinal axis L (7).

Preferably an accelerometer and gyroscope are employed in the electric toothbrush handle, and more preferably contained in the handle body. One non-limiting is example of a accelerometer and gyroscope, and used in the non-limiting example, is a MEMS sensor provided on a single chip (available from STMicroelectronics, Inc.). The example has this chip connected through I2C to a National Instruments, Inc. USB module, which in turn, is connected to the LAB-VIEW software programmed at a high level with the I2C. Although the data is not shown, the force measured is observed to be surprisingly sensitive by being able to detect the weight of the replaceable toothbrush head (at about 5 grams). Electrical noise can be reduced by using a printed circuit board (PCB).

It is generally beneficial to provide correction circuits for correcting the balance of sensitivities, temperature characteristics of the sensitivities, temperature drift, and so on of the 3-axis force sensor, gyroscope, and/or accelerometer in the respective axes. Furthermore, a band pass filter (low-pass filter) for removing noise may also be provided. Further still, noise may be reduced by smoothing the waveforms of the outputs from, for example, the accelerometer.

The receiver body may be comprised of varying materials or combination of materials. In one example, the receiver body has metal (e.g., aluminum) drive shaft extending (along the longitudinal axis) at least partially through, if not completely through, with plastic around the drive shaft. Alternatively the receiver body may use metal (e.g., aluminum) to surround the drive shaft. One skilled in the art will recognize that plastic does not have the same stiffness in compression and traction than, e.g., aluminum has. The strain gauges may take properties into account (e.g., electronically compensating and/or electronically taring before the user starts brushing with the device).

Processing Unit (PU) and Memory

Data (e.g., 3-axis force sensor data, and preferably 3-axis accelerometer and gyroscope data, and even measured impedance values) is processed by a processing unit (PU). The PU may be a part of the electric toothbrush handle, or remotely by a computing device, or two PUs are employed (one in the handle one and one remotely). Similarly memory may be part of the electric toothbrush handle, or be located remotely in a computing device, or two memories are employed (one in the handle and one remotely). The memory can store programs, algorithms, data, etc. and is in communication with the PU. The memory and the PU may each independently be embodied in any form and may be associated with each other in any form. Some non-limiting examples of the memory and the processor, as well as their association, may be found in US2013/0176750A1 at paragraphs 426 to 431. One advantage of having the PU (and memory) remote from the electric toothbrush handle is that costs can be minimized by leveraging the processing power of ubiquitous computing devices (such as smart phones, tablet computers, lap top computers, and the like). Lastly, the electric toothbrush handle or computing device may comprise a web interface configured to inter alia upload stored or processed data to a remote server (or download such data).

Data Transmitter/Data Receiver

Data, either processed data or unprocessed data, can be sent from the electric toothbrush handle by a transmitter. In turn, data can be received by the electric toothbrush handle by a receiver. Similarly, a computer device (remote from the electric toothbrush) may receive data from the electric toothbrush handle via a receiver and send data to the electric toothbrush handle via a transmitter. There are several ways data can be sent. One way is directly through a wire such as a USB port or IEEE 1394 (Firewire) port or the like. Another way is wirelessly through near field communications (such as Bluetooth™, IEEE 802.15.1) or Wi-FI or WiMAX or the like. Preferably the wireless communications are effective for ±2-5 meters. The communications can be by way of visible light, ultrasound, infrared light, radio frequency, and other communication technologies. Of course other wire-replacement communications hardware and software may be used, preferably with low power consumption. Another advantage of a system is a more desirable user interface including web sites and convenience of software updates and a larger display that a computing device will typically have. A computing device may be able to track historical results or compare to standards or other personal objectives of the user's oral hygiene goals, and the like.

Other Electronic Components

The electronic components, of the electric toothbrush herein, may be in communication with each other, the PU, or transmitter/receiver. As used herein, the term "in communication with" means there is data transmission between two elements connected by this term. The communication method may be of any form, including wireless communication or hard-wired communication. Some examples of the communication methods are discussed in, for example, US20130311278A at paragraphs 39 to 41.

The electric toothbrush handle may further comprise a timer. The timer is in communication with the processing unit (and optionally the memory) The timer may be configured for measuring a time duration at a given oral cavity position. A display may be provided in communication with the electric toothbrush handle or even on outside surface of the electric toothbrush handle (e.g., housing) viewable to the user. The display may be configured for displaying the time duration at each oral cavity position (e.g., defined tooth zone). The display may be integrated into the electric toothbrush handle or physically separate from the electric toothbrush handle (e.g., remote computing device). An indicator may also be provided in data communication with the electric toothbrush handle. The indicator may be configured for indicating whether the time duration is shorter or longer than a predetermined amount of time. The indicator may be integrated into the electric toothbrush handle or physically separate from the electric toothbrush handle or even as a part of the display.

To potentially increase the precision or accuracy of oral cavity position, the electric toothbrush of the present invention may have one or more electrode pairs disposed on the surface of the removeable attached replaceable toothbrush head. The electric toothbrush handle may have a frequency generator, an impedance measurement unit and a contact determination unit. The electrode pair is preferably disposed on the housing of the head (or the neck terminus) that contacts various oral area(s) during electric toothbrush's use in the oral cavity. The term "oral area", as used herein, refers to a distinct part or section inside an oral cavity, including but not limited to, cheek area, tongue area, saliva area, tooth area, gum area, hard palate area, soft palate area, and lip area.

The neck terminus may be of a bulbous shape there by providing a greater surface area to dispose the electrodes. Of course additional electrodes may be disposed elsewhere on the electric toothbrush to potentially enable even more precise contact information with a defined oral area (depending upon factors that may include cost constraints, extent of the surface area, and precision needed). Each of the electrodes may employ a conductive resin or metal material, and may be formed integrally with housing associated with the electric toothbrush or may be assembled/connected to, for example, the replaceable toothbrush head.

An impedance is formed between the electrode pair when electrified. Electricity is provided by way of the battery. The battery is in electrical communication with one or more of the electrical components of the device. The frequency generator is electrically connected to the electrode pair, for applying a voltage with at least two different frequencies between the electrode pair. The change in frequencies happens preferably within about 1 s, 500 ms, 50 ms, 10 ms, 5 ms, or even 1 ms. The impedance measurement unit is electrically coupled to the electrode pair, for measuring impedance values between the electrode pair at the different frequencies. The term "impedance value" is used herein the broadest sense to include any value that can be derived from assessing conductivity/dielectricity between electrodes including but not limited to impedance magnitude, impedance phase, relative permittivity, and combinations thereof.

It is observed that certain oral areas of the oral cavity have unique impedance signatures when impedance is assessed and compared at different voltage frequencies. Furthermore, these impedance signatures (at different voltage frequencies) are even more pronounced between oral areas at certain frequency ranges. Without wishing to be bound by theory, it is the unique conductivity/dielectricity of each oral area that provides for the unique impendence signature at different voltage frequencies (at frequency ranges). See P&G Case AA00951M (Appl. No. EP 14 17 8041) and AA00952M (Appl. No. EP 14 17 8035), where it is reported that cheek area, the tongue area and the saliva area have quite different impedance magnitudes at various frequencies and thus can be distinguished from each other. Oral cavity position can be improved by incorporating this impedance data to help determine oral cavity position of the electric toothbrush during operation. The frequency generator and the impedance measurement unit may be integrated into a printed circuit board (PCB). The electrodes may be connected to the PCB by way of conductors and/or lines.

The replaceable toothbrush head may further comprise at least one electrode pair (preferably two, three, or more electrode pairs) disposed on an outer (housing) surface (preferably at or near the head), with an impedance formed between the plurality of electrodes when electrified. The battery may be an electricity source. The electric toothbrush handle further contains a frequency generator in electrical communication to the electrode pair for applying a voltage with a least two different frequencies (alternatively three or more frequencies) between the electrode pair (s). The electric toothbrush handle further contains an impedance measurement unit electrically coupled to the electrode pair(s) for measuring impedance values between the electrode pair. Optionally the handle containing a transmitter for transmitting measured impedance values.

The aforementioned memory (either remote or contained in the electric toothbrush handle) may store a function, wherein the function correlates impedance values of a defined oral area. A "defined oral area" is a predetermined oral area of which the impedance value has been assessed and can be used as a reference. The aforementioned processor (either remote or contained in the electric toothbrush handle) may process the measured impedance values to the stored function so as to determine contact information of the electrode pair with the defined oral area. As used herein, the term "contact information" relates to whether a given surface of the replaceable toothbrush head, as defined by the location of the electrode pair disposed on the given surface, is contacting a defined oral area. Based on this information, an oral cavity position may be estimated (in a given point of time per the aforementioned timer). For example, if the rear side of the head (e.g., side opposing the oral cleaning or massaging elements) is contacting the cheek during brushing, it can be estimated that the oral cavity position of the head is between the cheek and the teeth with the oral cleaning or massaging elements (e.g., bristles) are facing the teeth of the user. The transmitter may transmit impedance values or contact information.

Figure 4:
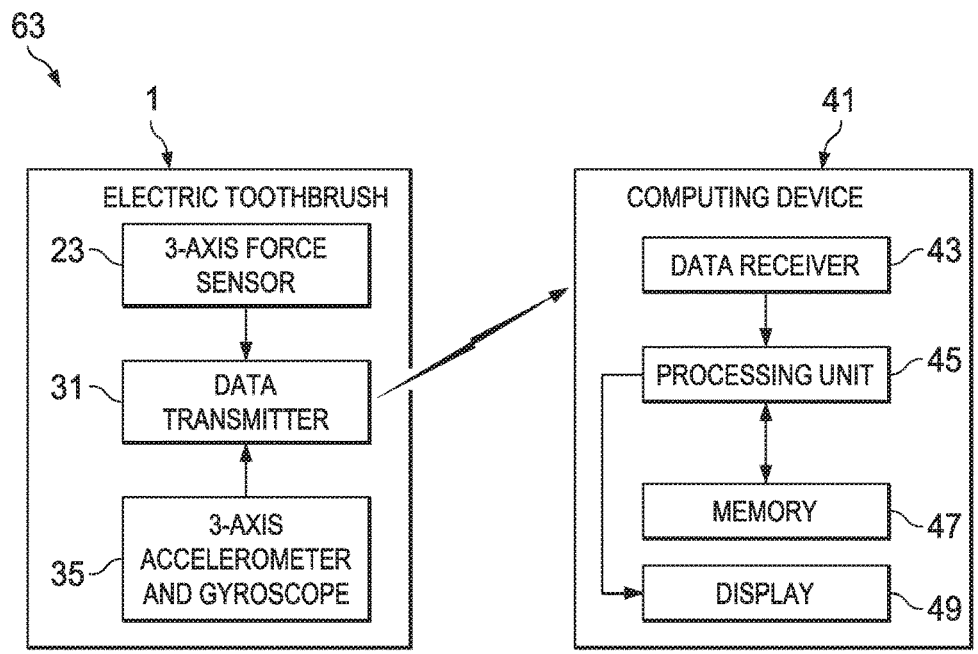
FIG. 4 is block diagram for determining oral cavity position of the electric toothbrush when the processing unit is located remotely from the electric toothbrush.

Turning to FIG. 4, a first system (63) is provided. This first system (63) comprises an electric toothbrush handle (20) or an electric toothbrush (1) in communication with a computing device (41). The electric toothbrush handle (20) or electric toothbrush (1) is as previously described, and notably has a 3-axis force sensor (23), operatively connected to the base portion (17), configured to obtain 3-axis force data for oral cavity position detection during operation, and has an accelerometer and gyroscope (35), contained within the handle body (11), configured to providing 3-axis accelerometer and gyroscope data force to help with oral cavity position detection during operation. A data transmitter (31), in communication with the 3-axis force sensor (23) and accelerometer and gyroscope (35), is configured for transmitting 3-axis force sensor data and 3-axis accelerometer and gyroscope data. A computing device (41) (remote from the electric toothbrush (1) or electric toothbrush handle (20)) has a data receiver (43) configured to receive transmitted 3-axis force sensor data and 3-axis accelerometer and gyroscope data. The computing device (41) also has a processing unit (45) configured to process the received data. The computing device (41) also has a memory (47) configured for storing data (processed and unprocessed). Lastly, the computing device (41) may also have a display (49) configured for displaying the stored data or processed data, wherein the processed data is oral cavity position detection of the electric toothbrush handle (20) or electric toothbrush (1) during operation.

Figure 5:
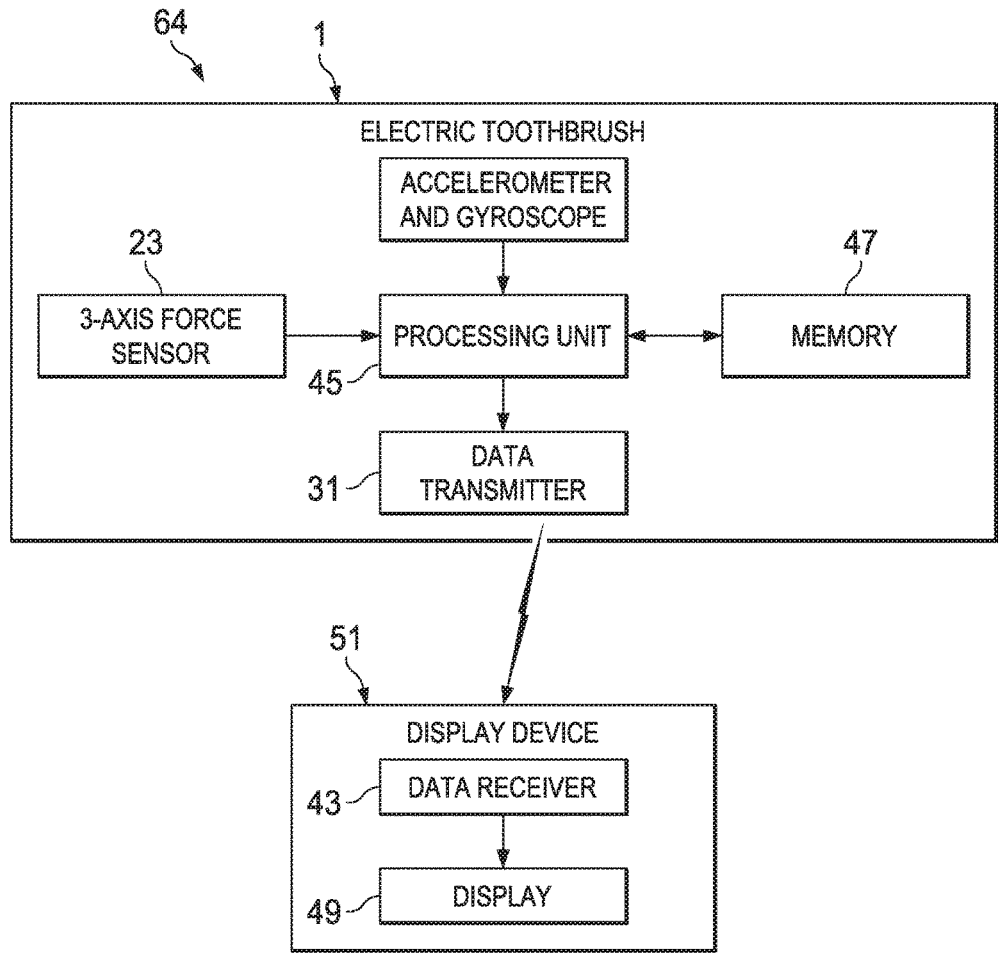
FIG. 5 is block diagram for determining oral cavity position of the electric toothbrush when a processing unit is located within the electric toothbrush.

FIG. 5 is a second system (64). This second system (64) comprises an electric toothbrush handle (20) or an electric toothbrush (1) in communication with a computing device (41). The principle difference between the second system (64) and the aforementioned first system (63) is the location of the processing unit (45). The second system (64) has the processing unit (45) in the toothbrush handle (20) or electric toothbrush (1). Still referring to FIG. 5, the electric toothbrush handle (20) or electric toothbrush (1) is as previously described, and notably has a 3-axis force sensor (23), operatively connected to the base portion (17), is configured to obtain 3-axis force data for oral cavity position detection during operation, and has an accelerometer and gyroscope (35), contained within the handle body (11), configured to providing 3-axis accelerometer and gyroscope data force to help determine oral cavity position detection during operation. The handle (20) or brush (1) has memory (47) for storing a function, wherein the function correlates 3-axis force sensor data and 3-axis accelerometer and gyroscope data of a defined oral cavity position. A processing unit (45), in communication with the 3-axis force sensor (23) and the accelerometer and gyroscope (35), is configured for processing obtained 3-axis force sensor data and 3-axis accelerometer and gyroscope sensor data to the stored function to determine oral cavity position detection during operation. The handle (20) or brush (1) further has a transmitter (31) for transmitting the determined oral cavity position. A display device (51) having a data receiver (43) receives the determined oral cavity position and display the determined oral cavity position on a display (49).

Oral Cavity Position Determination

Figure 6:
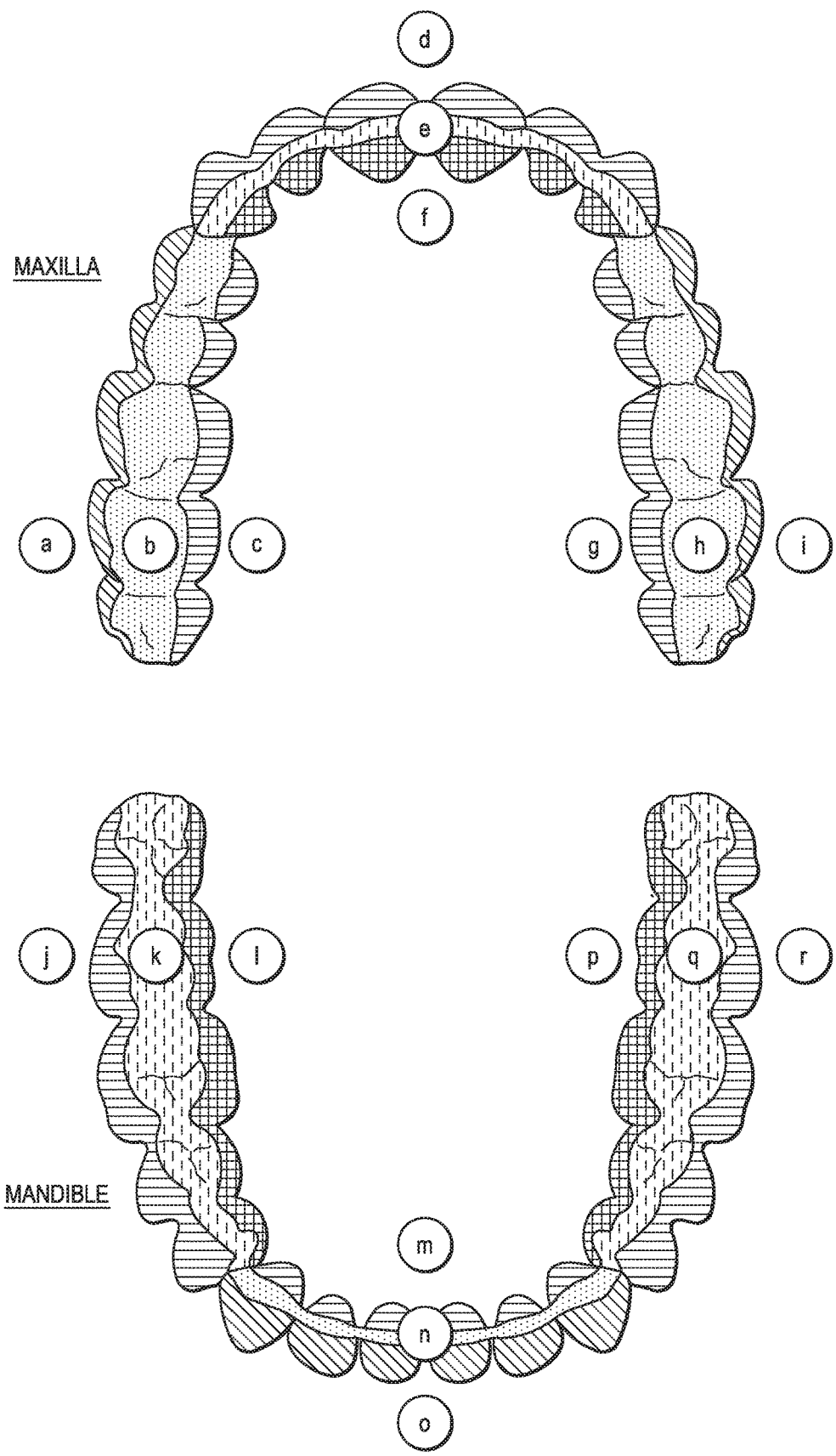
FIG. 6 is a diagram illustrating 18 tooth zones of oral cavity position.

The oral cavity position of the head (of the replaceable toothbrush head) may be defined by the oral cleaning or massaging elements side facing a tooth zone. The tooth zone means an area or a region on a tooth or teeth. The number and location of the tooth zone may vary based on a specific purpose. In one example, 18 tooth zones are divided around a user's teeth, as shown in FIG. 6. These 18 tooth zones are distinguished from each other by each one's unique location inside the oral cavity. These tooth zones include: buccal side of upper left back teeth (zone a), occlusal side of upper left back teeth (zone b), lingual side of upper left back teeth (zone c), front side of upper front teeth (zone d), occlusal side of upper front teeth (zone e), tongue side of upper front teeth (zone f), tongue side of upper right back teeth (zone g), occlusal side of upper right back teeth (zone h), cheek side of upper right back teeth (zone i), cheek side of lower left back teeth (zone j), occlusal side of lower left back teeth (zone k), tongue side of lower left back teeth (zone l), tongue side of lower front teeth (zone m), occlusal side of lower front teeth (zone n), front side of lower front teeth (zone o), tongue side of lower right back teeth (zone p), occlusal side of lower right back teeth (zone q), and cheek side of lower right back teeth (zone r).

Each of the 18 tooth zones as is identified by 3-axis force sensor data, preferably a combination of 3-axis force sensor data and 3-axis accelerometer and gyroscope data; alternatively a combination of 3-axis force sensor data and 3-axis accelerometer and gyroscope data, and contact information. The previously brushed tooth zone is taken into consideration to identify nearby tooth zones. This is based on an assumption that the user generally brushes teeth from one zone to another adjacent zone. An algorithm represented may be programmed into the PU and/or memory to distinguish all 18 tooth zones from each other. Therefore, all the 18 tooth zones may be distinguished by the present invention in a non-intrusive, precise and accurate way at low cost. Preferably the determined oral cavity position is selected from a plurality of tooth zones, more preferably at least 10 tooth zones, yet more preferably from 10 to 50 tooth zones, yet still more preferably from 12 to 25 tooth zones, alternatively about 18 tooth zones.

The aforementioned display may be provided as a user interface, for displaying and indicating information associated with the oral cavity position, so that the user may improve the brushing quality by optimizing their brushing procedure based on this information. In one example, the display is a diagram illustrating tooth zones (e.g., 18 tooth zones). A real-time feedback may be provided by lightening the tooth zone which has been brushed or is being brushed during brushing. Another real-time feedback may be provided by showing green if the tooth zone has received enough brushing and showing red if not enough brushing. Additionally, the tooth zone may blink if there is too much brushing. A summary feedback may be provided by showing how much time is used for each tooth zone during and/or after the brushing. An overall brushing result may be provided by showing if any tooth zone was missed or if all the tooth zones have been brushed properly. Such feedback would motivate the user to re-brush the tooth zones which have been missed or not brushed with enough time.

The aforementioned indicator may provides a visual, audio and/or physical signal to indicate the user to change the brushing tooth zone when the time used for one tooth zone is longer than a predetermined amount of time. A similar or complimentary approach may be used with brushing force with respect to any one tooth zone.

More information associated with the oral cavity position may be provided by a user interface to benefit the user, such as those disclosed in WO 2008060482 A2, paragraphs 24 to 26 of WO201177282 A1, and columns 15 to 16 of U.S. Pat. No. 8,479,341 B2. All the information may be displayed or indicated simultaneously or in sequence. The user may have a control on the information to be displayed or indicated. The display or indicator can be in communication to the PU.

Comparator

A comparator may be provided for comparing reference data to obtained 3-axis force data. Preferably an output device is coupled to the comparator for providing feedback to the user. The objective is to provide a toothbrush that can monitor the user's tooth brushing practices. During tooth brushing, the 3-axis force sensor obtains 3-axis force data, which may be recorded in memory or communicated to the comparator. The comparator may compare (either in real time or after the brushing episode) the obtained 3-axis force data to reference data and/or historical 3-axis force data. Data from the timer (e.g., time duration) and brushing force data (e.g., too much or too little force applied to a brushing zone) may be also be compared by the comparator. Positive feedback can be used to reinforce good tooth brushing practices and corrective feedback can be used to improve tooth brushing practices. These toothbrush practices may include oral cavity position determination and the amount of brushing force applied thereto. The PU may carry out the tasks of the comparator under the control of software. As previously discussed, the PU may be part of the toothbrush handle or be remote from the toothbrush (e.g., smart phone).

The feedback is configured to provide at least one least one output signal (alternatively three, four or more such output signals) to a user of electric toothbrush handle. The at least one output signal corresponds to at least one of a first plurality of conditions, wherein the at least one of a first plurality of conditions is selected from the following: not brushing a tooth zone, too little time brushing in a tooth zone, too much time brushing in a tooth zone, sufficient time brushing in a tooth zone, a lower end of a range of sufficient time brushing in a tooth zone, and an upper end of the range of sufficient time brushing in a tooth zone. Preferably a second output signal corresponds to at least of a second plurality of conditions, wherein the second plurality of conditions is selected from the following: too little applied force, too much applied force, a sufficient amount of force, a lower end of a range of sufficient force, and an upper end of the range of sufficient force. Examples of output signals may include tactile (e.g., vibration), audible, visual, or combinations thereof. One example of a visual signal is the previously described diagram illustrating 18 tooth zones. Further details and examples are described at U.S. Pat. No. 8,544,131 B2 at col. 3, 1. 54 to col. 4, 1. 32.

Manual Toothbrush

A manual toothbrush for providing oral cavity position detection during operation is also provided. The brush comprises: a handle body having a longitudinal axis; a head comprising one or more static oral care cleaning or massaging elements; a neck extending between the handle body and the head, wherein the head is distal the handle body; a battery (contained in the handle body). The manual toothbrush is characterized by at least a portion of the neck elastically deformable relative to said longitudinal axis; a 3-axis force sensor, in electrical communication with the battery, operatively connected to the elastically deformable portion of the neck or head, and configured to obtaining 3-axis force for oral cavity position detection during operation. Preferably a transmitter, in communication with the 3-axis force sensor, is configured to transmit 3-axis force sensor data remotely from the manual toothbrush.

Preferably the 3-axis force sensor of the manual toothbrush comprises at least three strain gauges, preferably at least four strain gauges, operatively and physically connected to a surface of the flexible portion of the neck or head. More preferably at least one of the three strain gauges provides compression or traction force data (along the longitudinal axis).

Preferably the manual toothbrush further comprising an accelerometer and gyroscope, contained within the handle body, configured to obtaining 3-axis accelerometer and gyroscope data force for oral cavity position detection during operation. Preferably the transmitter, in communication with the accelerometer and gyroscope, is configured to transmit 3-axis accelerometer and gyroscope data remotely from the manual toothbrush.

Other details of the manual toothbrush may be analogized to the earlier description provided for the electric toothbrush.

EXAMPLES

Example 1

Figure 7B:
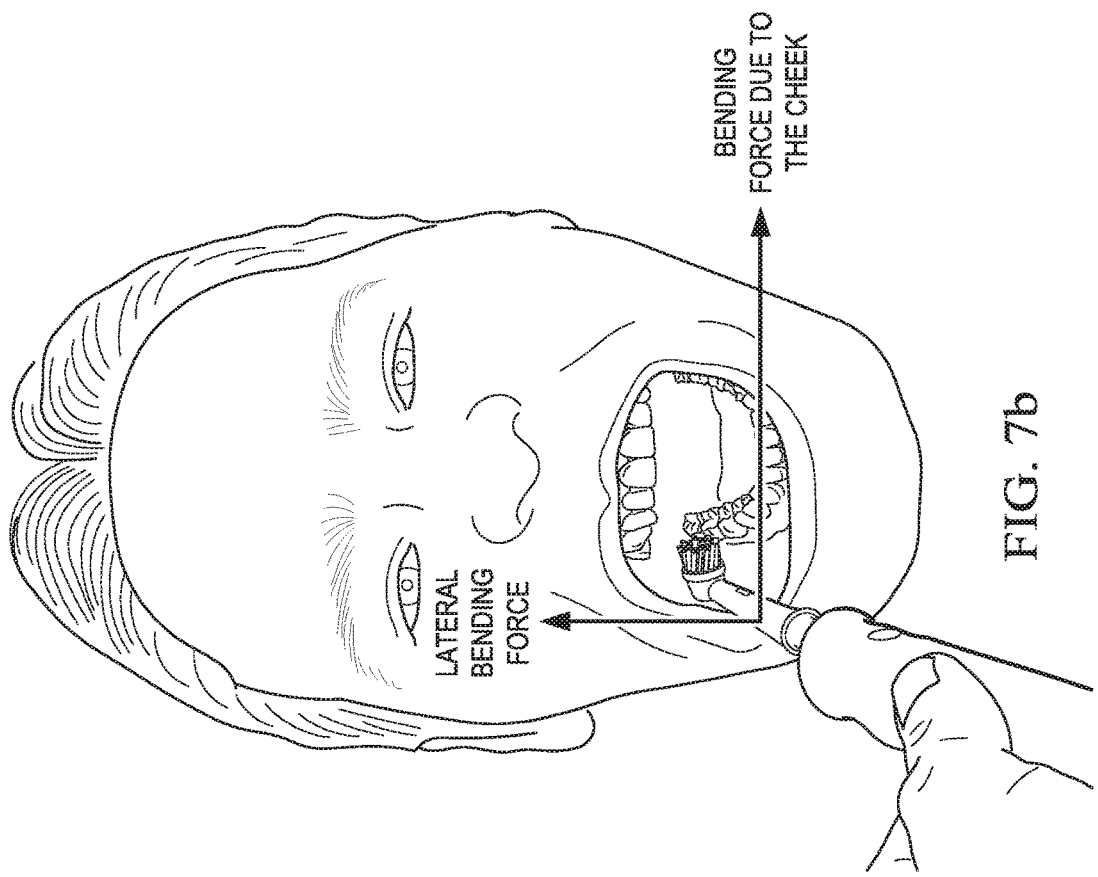
FIGS. 7a and 7b show the electric toothbrush starting in tooth zone j (of the 18 tooth zones of FIG. 6).
Figure 7A:
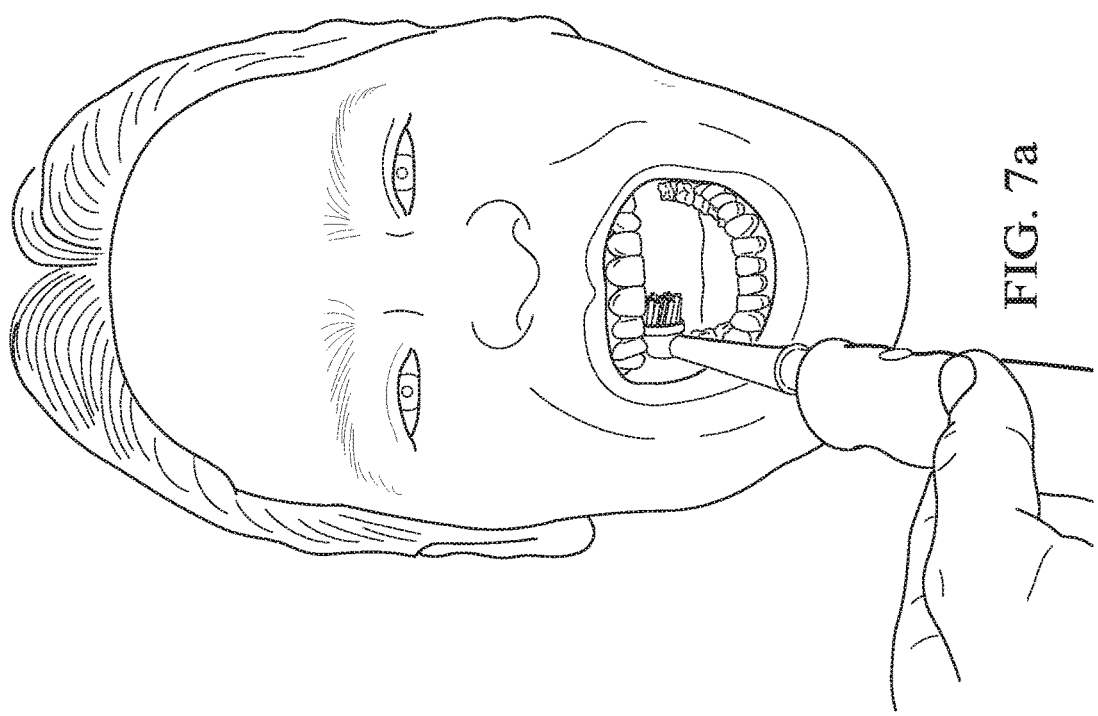

The following examples are provided using an electric toothbrush of the present invention. Reference is made to FIG. 6, and the 18 tooth zones (i.e., a-r). The electric toothbrush of the example has a head wherein the bristles are orthogonal to the longitudinal access. In example 1, the head of the electric toothbrush is inserted into the mouth as indicated in FIG. 7a, and the brushing operation is started in so called tooth zone j (out of 18 tooth zones). FIG. 7b shows the direction of the forces applied by the cheek on the head of the replaceable toothbrush head. The user has to push the cheek away with the head to move to the left part of the mouth, creating a normal bending force on the refill in the right direction as illustrated in FIG. 7b. The next step is moving the head down to reach zone j (and not zone a). This creates a lateral bending force going up. The combination of this 3-axis force sensor data coupled with the 3-axis accelerometer and gyroscope data indicate the head's bristles are looking to the right there by enabling the device to uniquely identify the oral cavity position as tooth zone j.

Example 2

Figure 8:
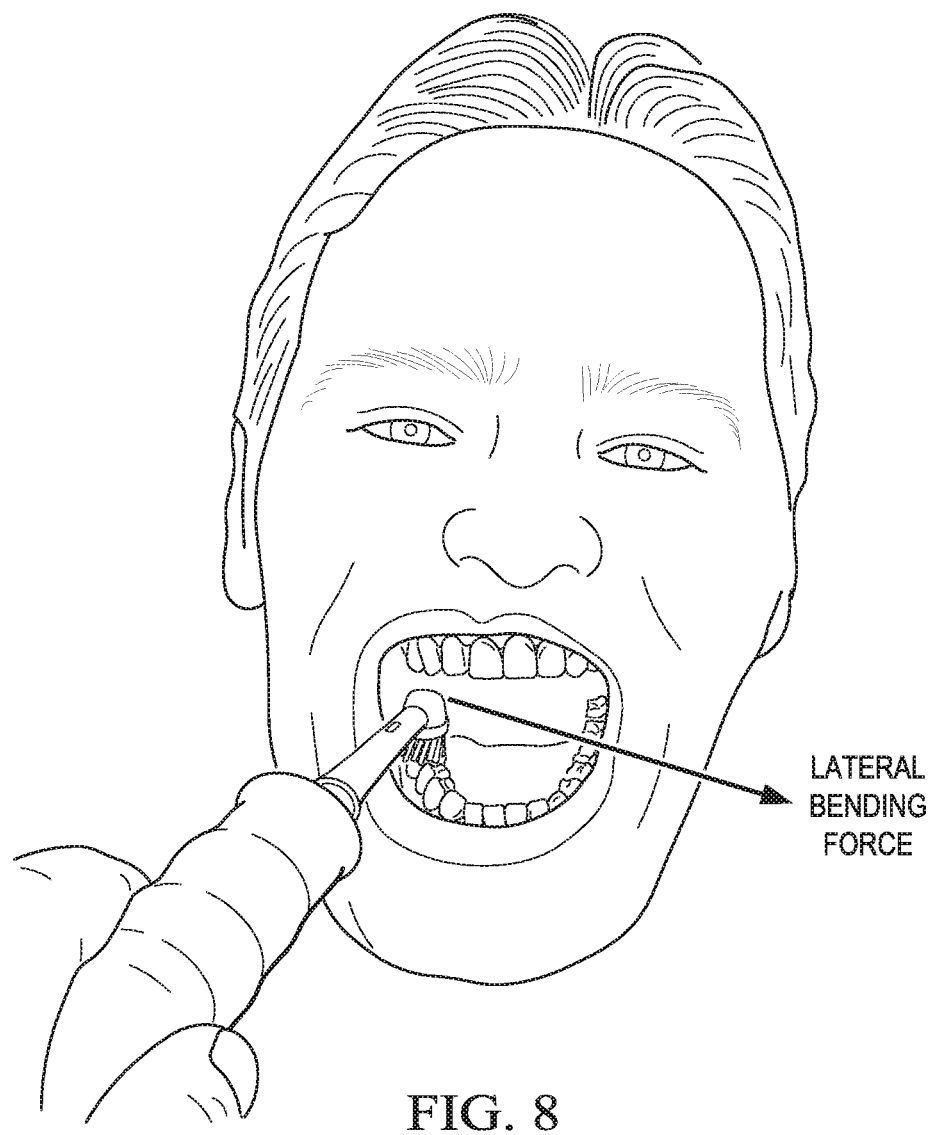
FIG. 8 shows the electric toothbrush in starting tooth zone k (of the 18 tooth zones of FIG. 6).

Example 2 illustrates when a user starts in tooth zone k. When a user starts in tooth zone k, the cheek or the impact on the teeth will apply a little force on the refill in the direction shown in FIG. 8. Because a lateral bending force is detected, no normal force from the cheek and also 3-axis accelerometer and gyroscope data indicating the bristles are facing down, the starting oral cavity position is tooth zone k.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush handle for providing oral cavity position detection during operation, the handle comprising:
   a handle body having a longitudinal axis L;
   a receiver body extending from the handle body along said longitudinal axis L, wherein the receiver body has:
   an engaging portion distal the handle body and configured to removably engage a replaceable toothbrush head; and
   a base portion opposing the engaging portion, wherein the base portion adjoins the handle body;
   an electric motor contained in the handle body;
   a drive shaft operatively connected to the electric motor and extending along the longitudinal axis L from the motor and at least partially into the receiver body;

wherein the receiver body is elastically deformable relative to said longitudinal axis L; and a three-axis force sensor operatively connected to the base portion and configured to obtain three-axis force data for oral cavity position detection during operation, wherein the three-axis force data comprises (a) lateral bending forces in at least one of an x-axis direction and a y-axis direction caused by elastic deformation of the receiver body and (b) traction or compression forces along the longitudinal axis, wherein the x-axis and y-axis directions are perpendicular to each other and to the longitudinal axis.

2. The handle of claim 1, wherein the three-axis force sensor comprises at least three strain gauges operatively and physically connected to a surface of the base portion.

3. The handle of claim 2, wherein the three-axis force sensor comprises at least four strain gauges operatively and physically connected to the surface of the base portion, wherein said surface of the base portion is an outside surface of the base portion but within a housing.

4. The handle of claim 2, wherein the at least three strain gauges are operatively and physically connected to the surface of the base portion.

5. The handle of claim 4, wherein the base portion has a cross section in a shape of a polygon; and wherein the cross section has a cross sectional area from about 20 mm$^2$ to about 30 mm$^2$.

6. The handle of claim 1, wherein the base portion has a cross sectional area from about 10 mm$^2$ to about 40 mm$^2$.

7. The handle of claim 1, further comprising an accelerometer and gyroscope contained within the handle body and configured to providing three-axis accelerometer and gyroscope data force for oral cavity position detection during operation.

8. The handle of claim 5, further comprising an accelerometer and gyroscope contained within the handle body and configured to providing three-axis accelerometer and gyroscope data force for oral cavity position detection during operation.

9. The electric toothbrush handle of claim 7, further comprising: a data transmitter, in communication with the 3-axis force sensor and accelerometer and gyroscope, configured for transmitting 3-axis force sensor data and the 3-axis accelerometer and gyroscope data.

10. The handle of claim 8, further comprising a data transmitter in communication with the three-axis force sensor and accelerometer and gyroscope, the data transmitter being configured for transmitting three-axis force sensor data and the three-axis accelerometer and gyroscope data.

11. The handle of claim 7, further comprising:
a memory for storing a function, wherein the function correlates three-axis force sensor data and three-axis accelerometer and gyroscope data of a defined oral cavity position;
a processing unit in communication with the three-axis force sensor and the accelerometer and gyroscope, configured for processing obtained three-axis force sensor data and three-axis accelerometer and gyroscope senor data to the stored function to determine oral cavity position detection during operation.

12. The handle of claim 11, further comprising a transmitter for transmitting the determined oral cavity position, wherein the determined oral cavity position is a plurality of tooth zones.

13. The handle of claim 10, wherein the accelerometer and the gyroscope are on a single chip.

14. The handle of claim 7, further comprising a comparator for comparing reference data to the obtained three-axis force data;
an output device coupled to the comparator for providing feedback to the user;
wherein the feedback is configured to provide at least one output signal;
wherein the output signal corresponds to at least one of a first plurality of conditions,
wherein the at least one of a plurality of conditions is selected from the following:
not brushing a tooth zone, too little time brushing in a tooth zone, too much time brushing in a tooth zone, sufficient time brushing in a tooth zone, a lower end of a range of sufficient time brushing in a tooth zone, and an upper end of the range of sufficient time brushing in a tooth zone.

15. The handle of claim 1, further comprising a replaceable toothbrush head having a head and a neck, wherein the neck extends between the engaging portion and the head, the head comprising one or more oral care cleaning or massaging elements, wherein the neck is removably attached to the engaging portion.

16. The handle of claim 10, further comprising a replaceable toothbrush head having a head and a neck, wherein the neck extends between the engaging portion and the head, the head comprising one or more oral care cleaning or massaging elements, wherein the neck is removably attached to the engaging portion.

17. The handle of claim 16, wherein the replaceable toothbrush head further comprises at least one electrode pair disposed on an outer surface of housing at or near the head, with an impedance formed between the plurality of electrodes when electrified,
wherein the handle further contains a frequency generator in electrical communication to the electrode pair for applying a voltage with at least two different frequencies between the electrode pair,
wherein the handle further contains an impedance measurement unit electrically coupled to the electrode pair for measuring impedance values between the electrode pair; and
wherein the handle contains a transmitter for transmitting measured impedance values.

18. A system comprising:
the electric toothbrush handle of claim 1; and
a computing device comprising
a data receiver configured to receive transmitted the three-axis force sensor data,
a processing unit configured to process the received data,
a memory configured for storing the processed data, and
a display configured for displaying the stored data or the processed data,
wherein the processed data is oral cavity position detection during operation.

* * * * *